United States Patent
Wozniak et al.

[19]

[11] Patent Number: 6,080,461
[45] Date of Patent: Jun. 27, 2000

[54] VISCOELASTIC MEMORY MEANS AND FLOW CONTROL VALVE AND USE THEREOF TO PRODUCE A SINGLE-USE, AUTO-DESTRUCT INJECTION DEVICE

[75] Inventors: John J. Wozniak, Columbia; Michael C. Robertson, Savage, both of Md.

[73] Assignee: The Johns Hopkins University, Baltimore, Md.

[21] Appl. No.: 08/209,673

[22] Filed: Mar. 10, 1994

Related U.S. Application Data

[62] Division of application No. 07/627,801, Dec. 14, 1990, abandoned.

[51] Int. Cl.$^7$ ................................................. B32B 3/02
[52] U.S. Cl. .................... 428/66.6; 128/919; 137/198; 137/199; 428/64.1; 428/66.4; 604/110; 604/187; 604/215; 604/218; 604/236; 604/238
[58] Field of Search ............................ 428/64, 65, 64.1, 428/66.4, 66.6; 128/919; 137/198, 199; 604/110, 187, 218, 215, 236, 238

[56] References Cited

U.S. PATENT DOCUMENTS

| | | | |
|---|---|---|---|
| 3,419,006 | 12/1968 | King | 128/268 |
| 3,429,794 | 2/1969 | Patterson | 204/159.14 |
| 3,757,779 | 9/1973 | Roviski | 604/190 |
| 4,226,236 | 10/1980 | Genese | 604/89 |
| 4,470,415 | 9/1984 | Wozniak | 128/334 R |
| 4,596,728 | 6/1986 | Yang et al. | 428/36 |
| 4,781,683 | 11/1988 | Wozniak et al. | 604/110 |
| 4,828,547 | 5/1989 | Sahi | 604/110 |
| 4,919,655 | 4/1990 | Cline | 604/110 |
| 5,000,735 | 3/1991 | Whelan | 604/110 |

FOREIGN PATENT DOCUMENTS

| | | | |
|---|---|---|---|
| 0112893 | 1/1969 | Denmark | 604/110 |
| 2622804 | 5/1989 | France | 604/110 |
| 1150980 | 5/1969 | United Kingdom | 604/110 |
| 8903231 | 4/1989 | WIPO | 604/110 |

OTHER PUBLICATIONS

Popular Science, p. 59, Dec. 1989.
Popular Science, p. 16, Jul. 1989.
J. Silverman, "Radiation Processing: The Industrial Applications of Radiation Chemistry", J. of Chem. Ed., pp. 168–173, Feb. 1981.
"One–time throwaway", Popular Science, p. 16 (Jul. 1989).
"Weapon against AIDS", Popular Science, p. 59 (Dec. 1989).

*Primary Examiner*—Nasser Ahmad
*Attorney, Agent, or Firm*—Francis A. Cooch

[57] ABSTRACT

Solid disks of polyethylene oxide are radiation crosslinked to instill viscoelastic memory. The disks are then pierced with a needle, heated, cooled and the needle removed to form disks containing a flow orifice in each which upon contact with water will revert to solid disks. A disk with a flow orifice made as just described when used as a memory flow control valve in a conventional injection device will produce a syringe with a single-use, auto-destruct capability. When the disk is inserted in a retainer in the flow channel of the injection device, a drug/vaccine can be drawn into the syringe and then expelled for a preselected time less than six minutes before the water in the drug/vaccine causes the flow orifice in the disk to close, the disk then reverting to its solid shape due to its viscoelastic memory.

18 Claims, 4 Drawing Sheets

FIG.4A
FIG.4B
FIG.4C
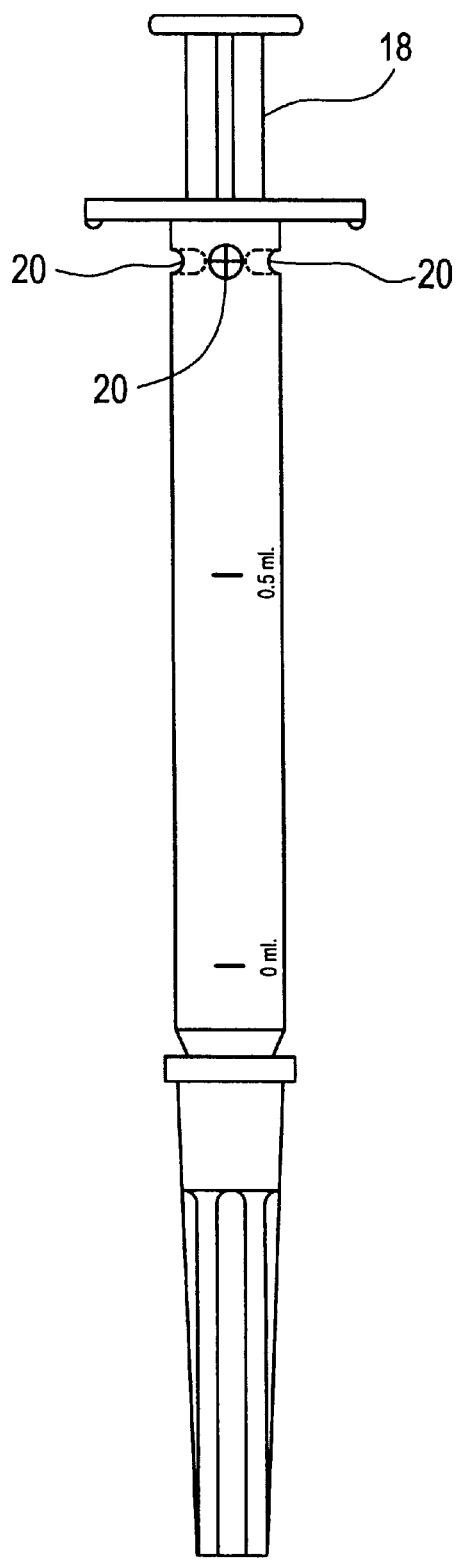
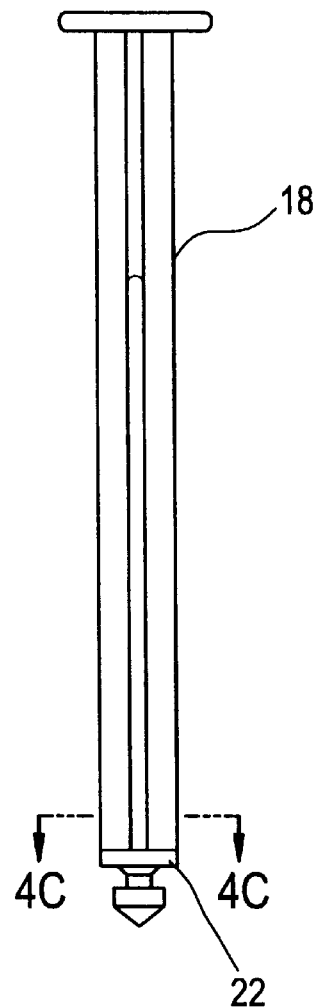
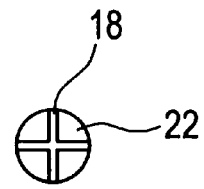

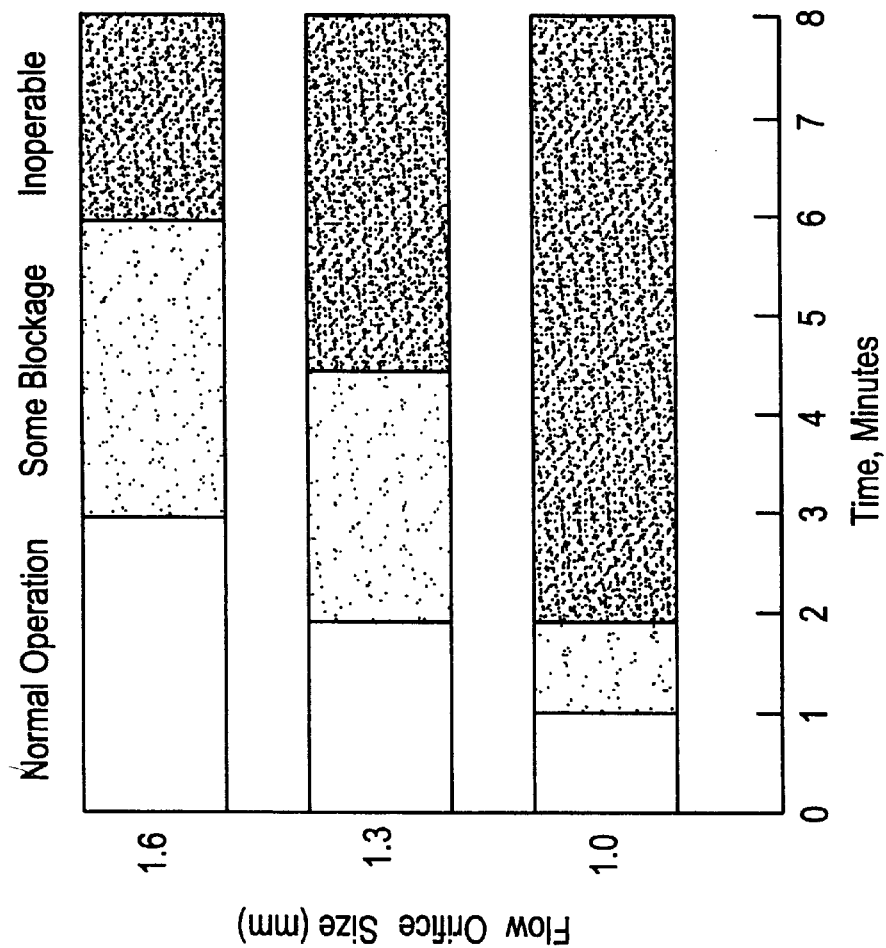

VISCOELASTIC MEMORY MEANS AND FLOW CONTROL VALVE AND USE THEREOF TO PRODUCE A SINGLE-USE, AUTO-DESTRUCT INJECTION DEVICE

This is a divisional of application Ser. No. 07/627,801 filed on Dec. 14, 1990, now abandoned.

BACKGROUND OF THE INVENTION

The invention relates generally to hydrophilic polymers with viscoelastic memory and to the use of such polymers, particularly polyethylene oxide (PEO), to produce single-use, auto-destruct (self-annulling) injection devices. Such injection devices, through the polymer of the invention, are rendered inoperative after a single injection without requiring any positive action on the part of the user.

The risk of the transmission of disease through the use of unsterile syringes and needles is of high concern to health care personnel. Childhood immunization requires some five injections, the safety of which must be assured if an immunization program is to achieve and maintain universal acceptance. The inadvertent transmission of disease during immunization is eliminated if one sterile syringe and one sterile needle are used for each injection. Consequently, it has become a priority among health care organizations to develop disposable injection devices that are inexpensive, cannot be used more than once, and can be introduced with little or no vaccinator retraining.

A single-use, self-annulling injection syringe has been disclosed and claimed in U.S. Pat. No. 4,781,683 ('683) which is incorporated herein by reference. The syringe of the '683 patent achieves single-use goals by the action of an insert pressed within the barrel of a conventional syringe with attached needle (cannula). The insert, in one embodiment, is composed of a crosslinked, hydrophilic polymer plug which swells upon contact with the water in the drug/vaccine being injected and thereby blocks the flow channel in the syringe. Therefore, the '683 patent provides for an inexpensive, single-use, and easy-to-use syringe.

Potential problems remain, however. The insert of the '683 patent can take up to 30 minutes to render the syringe inoperative which may be sufficient time to permit substantial reuse of the syringe. Further, if the hydrophilic plug is dehydrated, it might shrink to its original size rendering the syringe operative again. Finally, to enhance manufacturability, a different design for the plug/insert than those disclosed in the '683 patent is desirable.

SUMMARY OF THE INVENTION

The possible problems described above are avoided, to a great extent, through the practice of the invention. Illustratively, a hydrophilic polymer, e.g., polyethylene oxide, in the form of a solid disk is radiation crosslinked to instill viscoelastic memory. The solid disk of PEO is then pierced with a needle to form a hole or flow orifice in the center. The disk is then heated and cooled before the needle is removed. Thus, a viscoelastic memory means and, more particularly, a flow control valve (memory valve) is created which when used in an injection device produces a single-use, auto-destruct action as described below.

The disk-shaped memory valve with flow orifice in the center is press-fit into the cavity of a cup-shaped retainer where it is retained by a flange on the retainer's inside rim. A hole in the bottom of the retainer is aligned with the flow orifice in the memory valve. The memory valve-retainer unit is then pressed into an otherwise conventional injection device with the aligned hole and flow orifice being aligned with the flow channel created by the syringe barrel and the cannula (injection needle).

In use, the injection device is similar to a conventional syringe in appearance; in the filling, aspiration, and injection steps; and in the thumb force needed to make the injection. However, in a preselected time interval (depending on the memory valve's flow orifice size, but less than six minutes) after a water-based drug/vaccine first contacts and activates the memory valve, i.e., after fluid is first drawn into the injection device, the viscoelastic memory in the memory valve closes the flow orifice. By reverting to a solid, the disk-shaped memory valve renders the injection device inoperable.

Two design features prevent tampering or removal of the memory valve. First, the memory valve-retainer unit is locked into the syringe barrel by a ridge molded into the barrel. Second, removal of the plunger from the syringe barrel is prevented by a flange on the plunger and by one or more indentations pressed into the syringe barrel during the final step of assembly.

For a more complete appreciation of the invention, attention is invited to the following detailed description of a preferred embodiment of the invention taken with the figures of the drawings. The scope of the invention, however, is limited only through the claims appended thereto.

BRIEF DESCRIPTION OF THE DRAWINGS

FIG. 4, consisting of FIGS. 4a, 4b and 4c, illustrates the feature of the invention preventing removal of the plunger from the syringe barrel with FIG. 4c being a cross sectional view of the plunger of FIG. 4b taken along line 4c—4c.

FIG. 5 is a bar graph illustrating flow orifice size vs orifice closing time after contact with water.

DETAILED DESCRIPTION OF THE PREFERRED EMBODIMENT

Figure 1:
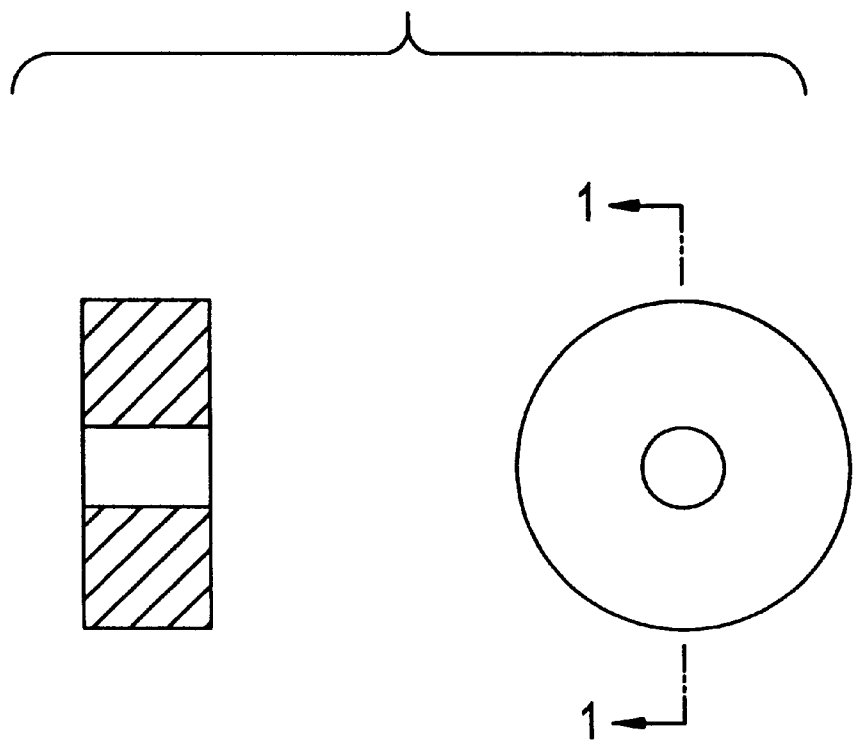
FIG. 1 consists of both a top view and a cross sectional view taken along line 1—1 of the top view of the disk-shaped memory flow control valve of the invention with flow orifice.

Viscoelastic memory or "shape-memory" is developed within the molecular structure of a polymer by virtue of exposure to high energy radiation (i.e., gamma rays or electron-beam) as discussed below and in U.S. Pat. Nos. 3,429,794 and 4,596,728, which are incorporated herein by reference. When polymers are exposed to radiation, two general types of reactions occur, scissions and crosslinking. Scission refers to degradation of the polymeric main chain structure without secondary reaction. Crosslinks form when a main chain molecule is broken and the resulting free radical reacts with a nearby molecule to form an interchain covalent carbon-carbon bond. When crosslinking dominates over scissions the reaction leads to a three dimensional network structure.

The crosslink structure is unaffected by heat while the portions of the polymer not incorporated in the crosslinks, the amorphous regions, melt when raised above the crystalline melt temperature. At temperatures below the crystalline melt temperature the irradiated polymer has the properties of a conventional plastic material, however, above its melt point the material acts as an elastomer (rubber-like).

When subject to a force in the elastomeric state, the material deforms temporarily to a second configuration, but returns to its original shape or first configuration upon removal of the force. If the polymer is cooled in the elastically distorted state or second configuration, the amorphous regions recrystallize and the material remains in a deformed state. If the deformed material is exposed to one of the normal solvents of the unirradiated material (or is reheated above the crystalline melt temperature), the material again becomes elastomeric and relaxes to release the internal stress thus returning to its original shape or first configuration. This is the basic principle behind the manufacture and use of the viscoelastic memory means and flow control valve (memory valve) made therefrom which is used to produce a single-use, auto-destruct injection device.

The preferred material for use in the viscoelastic memory means and flow control valve of the invention is the hydrophilic polymer, polyethylene oxide (PEO), a thermoplastic with the following repeating unit: $(CH_2-CH_2-O)_n$. The factor n, which is the number of repeating units combined to form the overall molecular structure, is called the degree of polymerization. For use in a single-use, auto-destruct injection device, PEO with a degree of polymerization n=4,500 to 180,000 or, equivalently and respectively, a molecular weight of $2 \times 10^5$ to $8 \times 10^6$ (The repeating unit has a molecular weight of 44; consequently, e.g., $44 \times 180,000 \approx 8 \times 10^6$.) is satisfactory with PEO with n=180,000 and a molecular weight of $8 \times 10^6$ being best in terms of memory valve strength, tolerance to heat and humidity, and workability.

The specific PEO used for the injection device of the invention is a Union Carbide water-soluble resin, POLYOX® WSR-309 NF. NF refers to the National Formulary grade of polymer production. Special care is taken in the polymerization of this grade to insure very low-order (ppm) contamination with any potential toxic residuals.

The viscoelastic memory means and flow control valve fabrication process begins by molding PEO into a first configuration of solid disks (~4.0 mm in diameter by ~1.65 mm thick). This is done using conventional thermoplastic injection molding processing.

Crosslinks are then formed in the solid disk inserts by exposure to radiation. In the actual processing, disks are placed in a chamber in which air has been purged and replaced with inert nitrogen gas. A nitrogen environment is necessary because the free radicals created by the irradiation can react with the oxygen in air and degrade the material. The chamber in which the inserts are placed is kept cool during the irradiation with a cooling water jacket. Cooling is necessary since the irradiation generates heat which could melt the PEO if not properly cooled.

The disks are exposed to cobalt-60 gamma rays (~1.25 MeV (million electron volt) energy level) at a rate of ~2.0 megarads (Mrads) per hour to a total dose of 5–12 Mrads and preferably 8–10 Mrads. The crosslinking may also be accomplished using electron-beam irradiation. The irradiation forms crosslinks which instill the disk memory valves with the preferred shape or first configuration as a solid.

Following the crosslinking step, the individual disks are pierced by and stacked on a sharp needle. Piercing is done at room temperature to reduce the tendency of the piercing process to dome the disks as the needle is forced through the material. Ideally, the disk should have flat opposite faces.

The needle is then placed in a low temperature (65° C.) oven for 10 to 15 minutes. Elevating the temperature brings the crosslinked PEO into its elastic state while each memory valve is distorted into the shape of a disk with a flow orifice through its center by virtue of the needle. The needle, stacked with inserts, is removed from the oven and allowed to cool naturally to room temperature. Cooling recrystallizes the amorphous regions of the PEO, locking the memory valve into the desired shape or second configuration of a disk with a flow orifice through its center as shown in FIG. 1. The memory valves are then removed from the needle.

Figure 2:
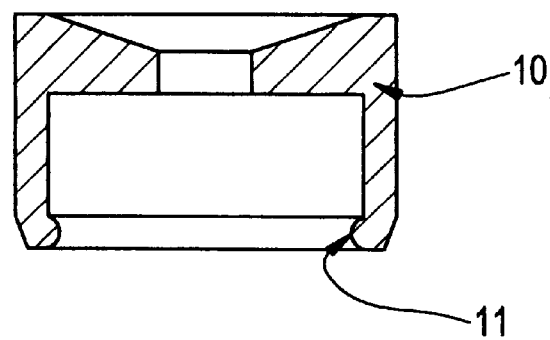
FIG. 2 is a cross sectional view of the retainer of the invention.

A retainer 10 (FIG. 2) is used to incorporate the viscoelastic memory valve into the barrel of a standard injection device to produce the desired single-use, auto-destruct syringe and to protect the memory valve from any tampering or attempt at removal. As shown in FIG. 2, the retainer 10 is cup-shaped with a cavity for receiving the memory valve and with a hole centered in the bottom of the cup. The concave face on the bottom of the retainer, i.e., on the opposite side of the hole from the cavity, is shaped to match the convex-shape tip of the internal piston end of the plunger in order to expel the maximum amount of the drug/vaccine drawn up into the syringe.

The memory valve 16 (see FIG. 3) is press-fit into the retainer 10 with the flow orifice in the disk (memory valve) being aligned with the hole in the retainer 10; a flange 11 protruding from the inside rim of the retainer 10 keeps the memory valve in the cavity. This operation reduces the memory valve and retainer to a single unit (memory valve-retainer unit).

Figure 3:
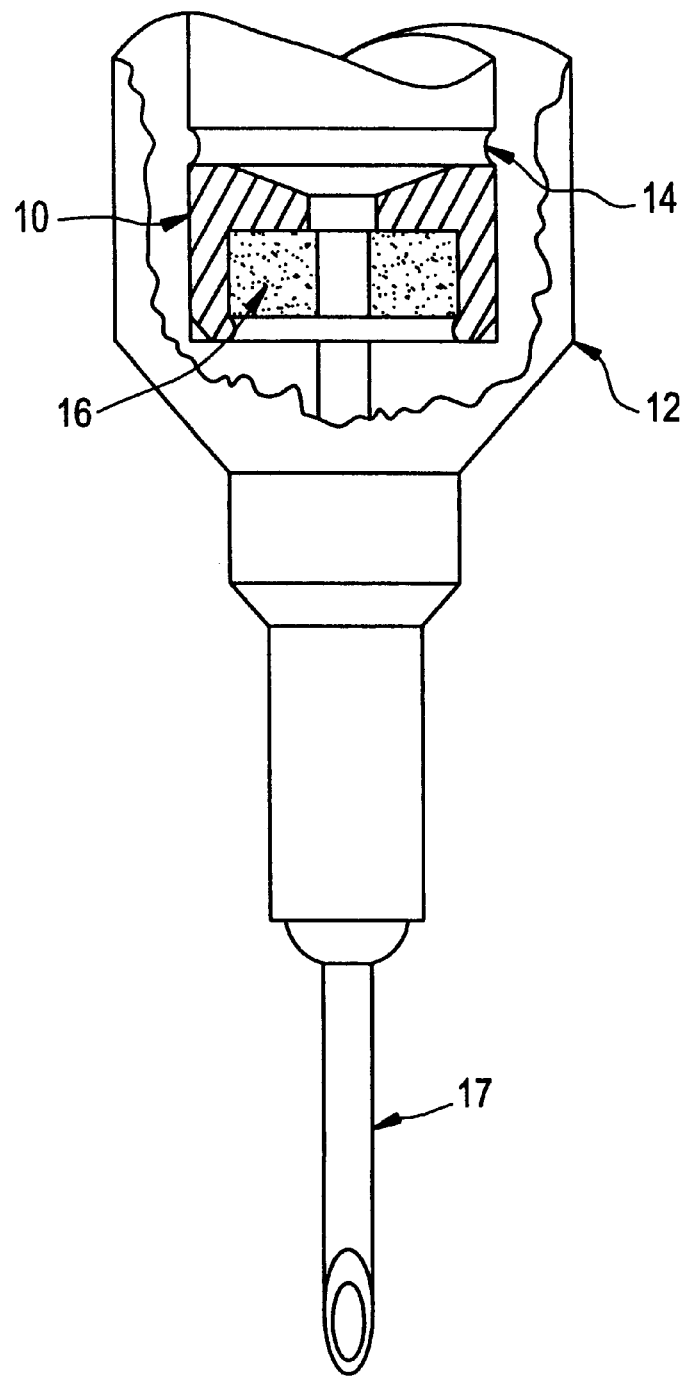
FIG. 3 is a cross sectional view of the memory valve-retainer unit of the invention shown in an injection device.

In the next step of assembly, a memory valve-retainer unit is inserted in the flow channel of an injection device. A detailed drawing of the memory valve-retainer unit and its positional relationship within the syringe barrel 12 is shown in FIG. 3.

The unit is placed into the plunger end of the syringe barrel 12 and is pressed forward the full length of the barrel. The outside diameter of the retainer 10 is sized to the same diameter as the syringe barrel diameter to ensure a tight frictional fit. It is the friction between the retainer 10 and syringe barrel 12 and a small ridge 14 molded into the inside of the barrel 12 that ensures that the memory valve 16-retainer 10 unit cannot be removed once it is installed. The follow-on steps of injection device manufacture (needle attachment, siliconization, and plunger insert) are the same as those for a traditional disposable plastic injection device.

As an added measure to inhibit tampering with the memory valve, the plunger 18 (FIGS. 4a, 4b, and 4c) cannot be removed from the syringe barrel 12. This is accomplished as the last step in assembly of the injection device as shown in FIG. 4a by pressing at least one, and preferably two or more, indentations 20 in the syringe barrel 12. A flange 22 molded on the plunger 18 shaft near the rubber piston end (see FIGS. 4b and 4c) contacts the indentations when the shaft is fully extended preventing removal of the plunger from the barrel.

Following printing and blister packaging, sterilization of the completed single-use, auto-destruct injection device is done using either the electron-beam or ETO (ethylene oxide) gas process. Either process is the same as that used in the case of a conventional syringe although, for the ETO sterilization, the processing levels of heat and humidity must be controlled within certain limits to ensure that the viscoelastic memory is not triggered to close the flow orifice. Cobalt-60 irradiation cannot be used for sterilization of the injection device of the invention as this process severely effects the crosslink network which alters the timing of the viscoelastic memory valve.

In operation, the flow orifice in the memory valve allows fluid to be drawn into and expelled from the injection device but, after a short period of time, the orifice closes by action of its viscoelastic memory to prevent any further fluid flow. The flow orifice closing response is a result of exposing the memory valve to water (a common base for most drugs/vaccines) which softens the crystalline structure. The softening enables the tension stored within the crosslink network to return the memory valve to its original solid shape or first configuration.

The initial diameter of the orifice is preferably at least twice as large as the internal lumen of the injection needle 17 (see FIG. 3) and, consequently, there is no restriction in the flow or thumb force needed to expel vaccine for the first time use. The flow orifice begins to close upon the initial filling of the syringe with a water-based drug but does not reach the final stage of being fully closed until a preselected time interval (less than six minutes and, preferably, between one and five minutes depending on the initial flow orifice diameter (see FIG. 5)).

In the final stage of closing there is increased flow resistance until the point when fluid can neither be expelled from nor drawn into the syringe. This produces the novel single-use, auto-destruct feature of the invention.

Drying the memory valve will not cause the flow orifice to return since a solid disk is the shape instilled during the radiation crosslinking step. This ensures that the single-use, auto-destruct feature is permanent and cannot be reversed by drying.

FIG. 5 is a graph which indicates the general relationship between PEO memory valve flow orifice diameter and the auto-destruct timing. For use in this specific application of the single-use, auto-destruct injection device, a one minute limit on the operational time was achieved by sizing the memory valve flow orifice to 0.88 mm.

What is claimed is:

1. A viscoelastic memory means comprising a hydrophilic polymer and produced by the steps of:

exposing the polymer to ionizing radiation sufficient to create intramolecular crosslinks within the polymer;

heating the polymer to substantially a crystalline melt temperature;

altering the shape of the polymer from a first configuration to a second configuration either before or after the heating step; and cooling the polymer while in the second configuration to reform the crystalline structure;

whereby the polymer will remain in the second configuration until exposed to a solvent of the polymer thereby causing the polymer to revert from the second configuration to the first configuration.

2. The memory means as recited in claim 1, wherein the hydrophilic polymer comprises polyethylene oxide.

3. The memory means as recited in claim 2, wherein the solvent comprises water.

4. The memory means as recited in claim 3, wherein the polyethylene oxide has a molecular structure having a degree of polymerization of between approximately 4,500 to 180,000 or, equivalently and respectively, a molecular weight of between approximately $2 \times 10^5$ to $8 \times 10^6$.

5. The memory means as recited in claim 4, wherein the polyethylene oxide is exposed to cobalt-60 gamma rays to a total dose of five to twelve megarads.

6. The memory means as recited in claim 5, wherein the polyethylene oxide reverts from the second configuration to the first configuration in a time interval less than six minutes.

7. The memory means as recited in claim 3, wherein the polyethylene oxide is exposed to cobalt-60 gamma rays to a total dose of five to twelve megarads.

8. The memory means as recited in claim 3, wherein the polyethylene oxide has a molecular structure having a degree of polymerization of between approximately 180,000 or a molecular weight of approximately $8 \times 10^6$.

9. The memory means as recited in claim 8, wherein the polyethylene oxide is exposed to cobalt-60 gamma rays to a total dose of eight to ten megarads.

10. The memory means as recited in claim 4, wherein the polyethylene oxide is exposed to cobalt-60 gamma rays to a total dose of eight to ten megarads.

11. The memory means as recited in claim 7, wherein the polyethylene oxide has a molecular structure having a degree of polymerization of approximately 180,000 or a molecular weight of approximately $8 \times 10^6$.

12. The memory means as recited in claim 7, wherein the polyethylene oxide is a water-soluble resin manufactured by Union Carbide designated POLYOX® WSR-309 NF.

13. The memory means as recited in claim 5, wherein the time interval is from one to five minutes.

14. A viscoelastic memory flow control valve for use in an auto-destruct injection device comprising the memory means as recited in claim 5.

15. The memory flow control valve as recited in claim 14, wherein the time interval is from one to five minutes.

16. The memory flow control valve as recited in claim 14, wherein the first configuration comprises a solid and the second configuration comprises a solid with a flow orifice.

17. The memory flow control valve as recited in claim 16, wherein the solid is a disk.

18. The memory flow control valve as recited in claim 17, wherein the flow orifice is at least twice as large as the internal lumen of the injection needle.

* * * * *